(12) United States Patent
Berthon-Jones et al.

(10) Patent No.: US 6,755,193 B2
(45) Date of Patent: *Jun. 29, 2004

(54) ADJUSTMENT OF VENTILATOR PRESSURE-TIME PROFILE TO BALANCE COMFORT AND EFFECTIVENESS

(75) Inventors: Michael Berthon-Jones, Leonay (AU); Peter Bateman, Concord (AU); Gordon Malouf, Gymea Bay (AU)

(73) Assignee: ResMed Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/424,344

(22) Filed: Apr. 28, 2003

(65) Prior Publication Data

US 2003/0192544 A1 Oct. 16, 2003

Related U.S. Application Data

(63) Continuation of application No. 09/518,101, filed on Mar. 3, 2000, now Pat. No. 6,553,992.

(51) Int. Cl.⁷ .............................................. A61M 16/00
(52) U.S. Cl. ............................... 128/204.18; 128/204.33
(58) Field of Search ........................ 128/200.24, 204.18, 128/204.21, 204.22, 204.23, 204.26, 205.23, 203.12, 207.14; 600/529, 533, 538

(56) References Cited

U.S. PATENT DOCUMENTS

| | | | |
|---|---|---|---|
| 4,036,221 A | 7/1977 | Hillsman et al. | |
| 4,155,356 A | 5/1979 | Venegas | |
| 4,448,192 A | 5/1984 | Stawitcke et al. | |
| 4,776,333 A | 10/1988 | Miyamae | |
| 5,134,995 A | 8/1992 | Gruenke et al. | |
| 5,165,398 A | 11/1992 | Bird | |
| 5,303,698 A | 4/1994 | Tobia et al. | |
| 5,331,995 A | 7/1994 | Westfall et al. | |
| 5,503,146 A | 4/1996 | Froehlich et al. | |
| 5,540,220 A | 7/1996 | Gropper et al. | |
| 5,669,379 A | 9/1997 | Somerson et al. | |
| 5,735,267 A | 4/1998 | Tobia | |
| 5,865,173 A | 2/1999 | Froehlich | |
| 5,884,622 A | 3/1999 | Younes | |
| 5,931,160 A | 8/1999 | Gilmore et al. | |
| 6,082,357 A | 7/2000 | Bates et al. | |
| 6,135,105 A | 10/2000 | Lampotang et al. | |
| 6,135,106 A | 10/2000 | Dirks et al. | |
| 6,152,129 A * | 11/2000 | Berthon-Jones | 128/200.24 |
| 6,158,432 A | 12/2000 | Biondi et al. | |
| 6,273,088 B1 | 8/2001 | Hillsman | |
| 6,305,372 B1 | 10/2001 | Servidio | |
| 6,532,956 B2 * | 3/2003 | Hill | 128/204.18 |
| 6,532,957 B2 * | 3/2003 | Berthon-Jones | 128/204.21 |
| 6,553,992 B1 * | 4/2003 | Berthon-Jones et al. | 128/204.23 |
| 6,575,163 B1 * | 6/2003 | Berthon-Jones | 128/204.18 |

FOREIGN PATENT DOCUMENTS

| | | | | |
|---|---|---|---|---|
| EP | 0 671 181 A | | 9/1995 | |
| EP | 9710868 | | 3/1997 | |
| WO | WO 98/12965 | * | 4/1998 | 128/204.18 |
| WO | WO 99 24099 A | | 5/1999 | |
| WO | WO 99 61088 A | | 12/1999 | |

* cited by examiner

Primary Examiner—Aaron J. Lewis
Assistant Examiner—Teena Mitchell
(74) Attorney, Agent, or Firm—Gottlieb, Rackman & Reisman, P.C.

(57) ABSTRACT

The invention is a ventilator whose servo-controller adjusts the degree of support by adjusting the profile of the pressure waveform as well as the pressure modulation amplitude. As the servo-controller increases the degree of support by increasing the pressure modulation amplitude, it also generates a progressively more square, and therefore efficient, pressure waveform; when the servo-controller decreases the degree of support by decreasing the pressure modulation amplitude, it also generates a progressively more smooth and therefore comfortable pressure waveform.

28 Claims, 2 Drawing Sheets

ADJUSTMENT OF VENTILATOR PRESSURE-TIME PROFILE TO BALANCE COMFORT AND EFFECTIVENESS

This application is a continuation of co-pending U.S. patent application Ser. No. 09/518,101, filed on Mar. 3, 2000, now U.S. Pat. No. 6,553,992.

FIELD OF THE INVENTION

This invention relates to the field of mechanical ventilation, and more particularly to machines and methods for providing a patient with ventilatory support.

BACKGROUND

Conventional ventilators provide ventilatory support by utilizing a number of different pressure-time profiles. In its simplest form, a ventilator delivers airflow at a fixed rate (or some other fixed function of time such as sinusoidally), and the airway pressure increases passively as a function of the mechanical properties of the patient's respiratory system. Such a ventilator is in general suitable only for a paralyzed and sedated patient who cannot change his/her ventilation at will. Also, the system is intolerant of leak, so is unsuitable for non-invasive (mask) ventilation.

A bilevel ventilator uses a square pressure-time waveform:

$$P=P_{0+A}, f>0$$

$$P=P_0, \text{otherwise}$$

where $P_0$ is an end expiratory pressure, chosen to splint the upper and lower airways and alveoli, A is a fixed pressure modulation amplitude chosen to supply a desired degree of support, and f is respiratory airflow. Here, and throughout what follows, inspiratory flow is defined to be positive, and expiratory flow is defined to be negative. With bilevel support, the patient can breathe as much or as little as he wishes, by using greater or lesser effort, and the system is somewhat less affected by leak. Some known ventilators, for example, the Servo 300 available from Siemens Medical, Iselin, N.J., and the VPAP-ST from ResMed, San Diego Calif., have an adjustment for changing the initial rate of rise of pressure, with the intention of providing a more comfortable waveform by using a slower rate of rise. In such prior art, the clinician selects a particular waveform, but thereafter the waveform does not change, and there is no automatic adjustment of the waveform.

Moving on in complexity, a proportional assist ventilator provides pressure equal to an end expiratory pressure $P_0$ plus a resistance R multiplied by respiratory airflow, plus an elastance E multiplied by the time integral of respiratory airflow:

$$P=P_0+Rf+E\int f\,dt, f>0$$

$$P=P_0+Rf, \text{otherwise}$$

(where the integral is from the time of start of the current inspiration to the current moment) in which the resistance R is chosen to unload some or all of the resistive work of breathing, and the elastance E is chosen to unload some or all of the elastic work of breathing (that is to say, the Rf term provides a pressure increment to offset some or all of the effort required to get air to flow through the mechanical passageways, and the integral term provides some or all of the pressure required to overcome the elastic recoil or springiness of the lungs and chest wall). A proportional assist ventilator amplifies patient effort, delivering a natural-feeling waveform, and it is easier for the patient to increase or decrease his ventilation than in the case of bilevel support. However, a proportional assist ventilator is disadvantageous for a patient with abnormal chemoreflexes, as inadequate support is provided during pathological reductions in effort such as central apneas and hypopneas.

Another approach is to provide a pressure-time profile that is continuous function of phase in the respiratory cycle:

$$P=P_0+A\Pi(\Phi),$$

where $\Pi(\Phi)$ is a waveform template function, for example, as shown in FIG. 1, and $\phi$ is the phase in the respiratory cycle. In FIG. 1, the waveform template is a raised cosine during the inspiratory part of the cycle, followed by a quasi-exponential decay during the expiratory portion. This shape will produce a quasi-normal and therefore comfortable flow-time curve if applied to a passive patient with normal lungs.

For example, a servo-ventilator can be constructed by setting the pressure modulation amplitude A to:

$$A=-G\int(0.5|f|-V_{TGT})dt,$$

where G is a servo gain (for example, 0.3 cmH$_2$O per L/min per second), $V_{TGT}$ is a desired target ventilation (e.g., 7.5 L/min), and the integral is clipped to lie between $A_{MIN}$ and $A_{MAX}$ (for example, 3 and 20 cmH$_2$O) chosen for comfort and safety. A servo-ventilator has the advantage of guaranteeing a specified ventilation. By setting $A_{MIN}$ to be non-negative, the patient can at will comfortably breathe more than the target ventilation, but in the event of a failure of central respiratory drive, the device will guarantee at least a ventilation of $V_{TGT}$.

Finally, the advantages of using a waveform template can be combined with resistive unloading:

$$P=P_0+Rf+A\Pi(\Phi),$$

where $$A=-G\int(0.5|f|-V_{TGT})dt, 0<=A_{MIN}<=A<=A_{MAX}$$

as before, giving yet more comfort to an awake patient than in the case previously considered, yet without losing a guaranteed minimum ventilation of $V_{TGT}$.

A disadvantage of the pressure waveform template shown in FIG. 1 is that it is less efficient than a square wave. That is to say, for any given amplitude it provides less ventilatory support than a square wave. The waveform of FIG. 1 has only half the area of a square wave of the same amplitude. This can be a problem in patients who require a very high degree of support, or in the case of mouth leak, where in order to provide a desired pressure modulation amplitude at the glottic inlet, a much higher pressure modulation amplitude must be supplied at the mask. The use of pure resistive unloading is similarly inefficient for the same reason: the area under the pressure-vs-time curve is only half that of a square wave of the same amplitude. Even the combination of the smooth waveform tempate with resistive unloading is less efficient than a square wave of the same amplitude.

It is a general object of our invention to provide a pressure support ventilator that offers the advantages of using a smooth pressure waveform template while at the same time compensating for its disadvantages.

It is another object of our invention to balance comfort and effectiveness in a ventilator.

SUMMARY OF THE INVENTION

One broad concept implemented by the invention is to change the pressure waveform in a way that makes an advantageous trade-off between comfort and efficiency, using a more efficient but less comfortable waveform only when needed.

One aspect of the invention is a ventilator whose servo-controller adjusts the degree of support by adjusting the profile of the pressure waveform, preferably while also adjusting the pressure modulation amplitude.

In particular, the servo-controller increases the degree of support by increasing the pressure modulation amplitude, and also by generating a progressively more square, and therefore efficient, pressure waveform; the servo-controller decreases the degree of support by decreasing the pressure modulation amplitude, and by generating a progressively more smooth and therefore comfortable pressure waveform. The changes in amplitude and squareness can be performed sequentially, or partially or completely simultaneously.

BRIEF DESCRIPTION OF THE FIGURES

Further objects, features and advantages of the invention will become apparent upon consideration of the following detailed description in conjunction with the drawing, in which.

DETAILED DESCRIPTION OF THE INVENTION

Figure 2:
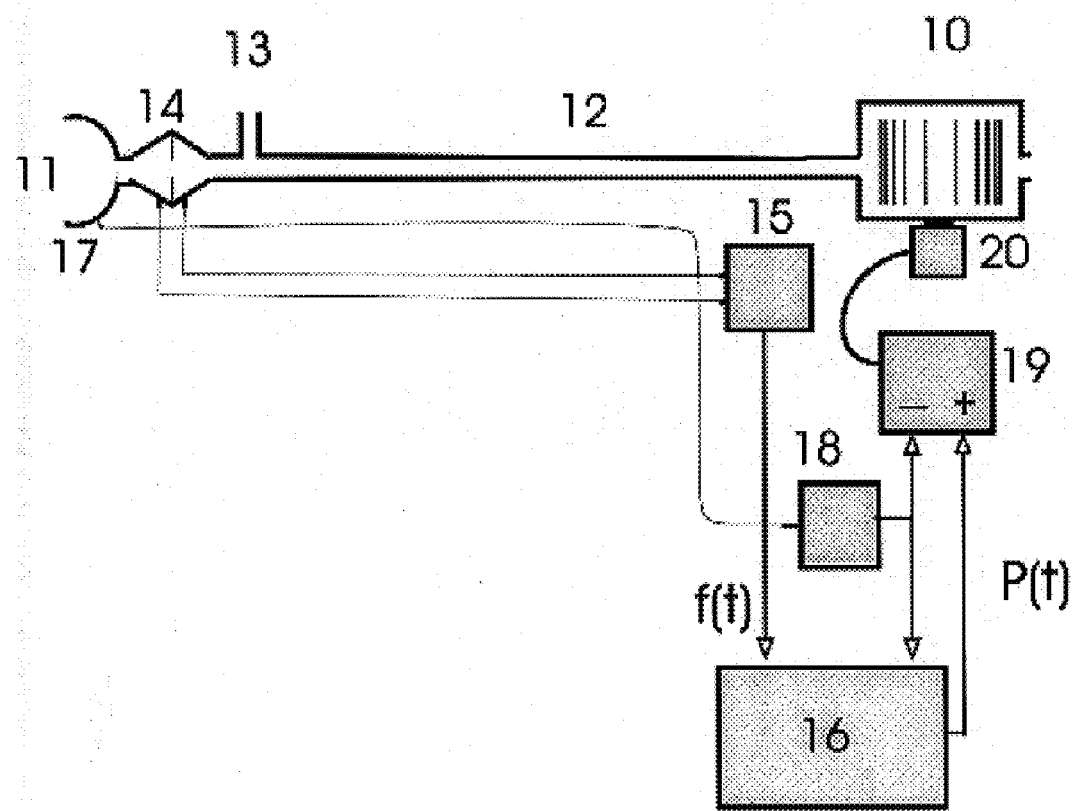
FIG. 2 depicts illustrative apparatus for implementing the method of the invention.

Suitable apparatus for implementing the invention is shown in FIG. 2. The apparatus provides breathable gas at controllable positive pressure to a patient's airway. In the drawing, a blower 10 supplies breathable gas to a mask 11 in communication with a patient's airway via a delivery tube 12 and exhausted via an exhaust 13. Airflow at the mask 11 is measured using a pneumotachograph 14 and a differential pressure transducer 15. The mask flow signal f(t) from the transducer 15 is then sampled by a microprocessor 16. Mask pressure is measured at the port 17 using a pressure transducer 18. The pressure signal from the transducer 18 is then sampled by the microprocessor 16. The microprocessor sends an instantaneous mask pressure request (i.e., desired mask pressure) signal P(t) to a servo-controller 19, which compares the pressure request signal with the actual pressure signal from the transducer 18 to control a fan motor 20. Microprocessor settings can be adjusted via a serial port, not shown.

It is to be understood that the mask could equally be replaced with a tracheotomy tube, endotracheal tube, nasal pillows, or other means of making a sealed connection between the air delivery means and the patient's airway.

The microprocessor accepts the mask airflow and pressure signals, and from these signals determines the instantaneous flow through any leak between the mask and patient, by any convenient method. For example, the conductance of the leak may be estimated as the instantaneous mask airflow, low-pass filtered with a time constant of 10 seconds, divided by the similarly low-pass filtered square root of the instantaneous mask pressure, and the instantaneous leakage flow may then be calculated as the conductance multiplied by the square root of the instantaneous mask pressure. Respiratory airflow is then calculated as the instantaneous mask airflow minus the instantaneous leakage flow.

Throughout the following discussion, the phase in the respiratory cycle $\Phi$ is taken as varing between zero and 1 revolution, with zero corresponding to start of inspiration and 0.5 corresponding to start of expiration.

Figure 1:
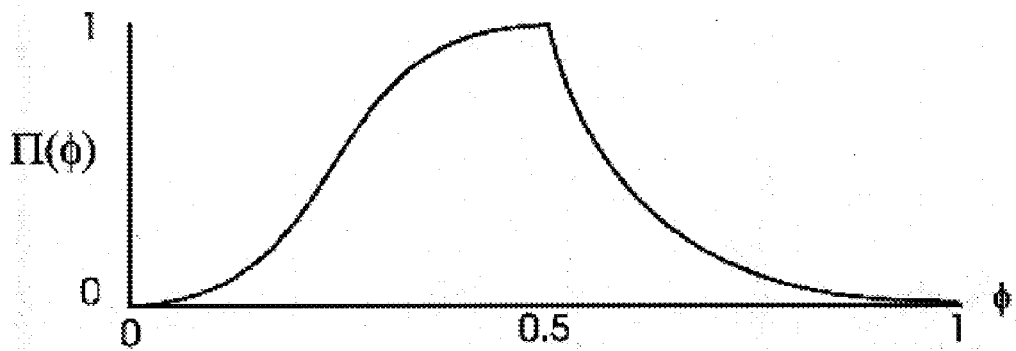
FIG. 1 depicts a smooth and comfortable ventilator waveform template function.

The desired mask pressure is described by the following equations:

$$P = P_0 + Rf + A\Pi(\Phi)$$

where:

$P_0$ is a desired end expiratory pressure chosen to splint the upper and lower airways or alveoli, or to reduce cardiac preload or afterload, for example, 5 cmH$_2$O;

R may be zero, but is preferably any value less than the patient's actual airway resistance;

f is respiratory airflow, measured, for example, using a pneumotachograph in the mask, and correcting for leak, for example, as described in the commonly owned International Publication referred to above;

$\Phi$ is the phase in the patient's respiratory cycle;

$\Pi(\Phi)$ is a pressure waveform template, initially set to be similar to that shown in FIG. 1, for example, comprising a raised cosine followed by an exponential decay.

In a very simple form, suitable for a patient who is making no spontaneous efforts, or in whom the spontaneous efforts can be ignored, the phase $\Phi$ simply increases linearly with time, modulo 1 revolution. In a preferred form, the phase $\Phi$ is calculated, for example, from the respiratory airflow f using fuzzy logic as taught in the commonly owned International Publication No. WO 98/12965 entitled "Assisted Ventilation to Match Patient Respiratory Need," referred to above.

An example of a smooth and comfortable pressure waveform template $\Pi(\Phi)$ is shown in FIG. 1. This particular waveform consists of a raised cosine followed by a quasi-exponential decay. (Unlike a true exponential decay, the waveform of FIG. 1 falls exactly to zero by the end of expiration, so that there is no step change at the start of the next breath.)

The first reason why the waveform of FIG. 1 is more comfortable than a traditional square wave is that the more sudden changes in pressure associated with a square wave are more intrusive than the smoother changes in pressure of FIG. 1.

The second reason why the waveform of FIG. 1 is more comfortable, whereas a traditional square wave is less comfortable, relates to precise synchronization of the delivered pressure to the patient's own muscular efforts. The more precise the synchronization, the more comfortable the waveform. The term R f in the equation $$P = P_0 + Rf + A\Pi(\Phi)$$

given above can be adjusted to obviate some or most of the effort required to unload resistive work. By a suitable choice of the amplitude A, and a suitable waveform $\Pi(\Phi)$, the term A $\Pi(\Phi)$ can be adjusted to unload most of the normal or pathological elastic work at the eupneic tidal volume, or alternatively at a minimum desired tidal volume, leaving the patient free to breathe deeper if he wishes. The reason for this is that a eupneically breathing subject's inspiratory flow-time curve is quasi-sinusoidal, and therefore the elastic component of effort, which is proportional to the integral of flow, is a raised cosine. For this reason, the waveform of FIG. 1 has a raised cosine during inspiration. During early expiration, a normal subject's muscular effort does not drop instantaneously to zero, but remains active some time into expiration, decaying gradually, which maintains a high lung volume longer than would otherwise be the case, thereby helping keep the alveoli inflated, and also providing a smoother movement of the chest wall. For this' reason; the waveform of FIG. 1 has a quasi-exponential decay during expiration. An additional advantage of the waveform of FIG. 1 over a square wave is that small errors in timing of the start of inspiration produce negligible errors in the delivered pressure, whereas with a square wave, a timing error causes the delivered pressure to be wrong by the entire amplitude of the waveform. Therefore, the waveform of FIG. 1 will feel better synchronized to the subject's efforts than a square wave.

Primary interest is in waveform templates which are nondecreasing during the inspiratory half of the cycle, nonincreasing during the expiratory half, and with the first derivative defined everywhere except at the transitions between inspiration and expiration and vice versa. Of particular importance are waveform templates which are families of functions indexed by a single smoothness parameter K, which can for concreteness take values between zero (least smooth, or most square) and 1 (most smooth). The maximum absolute value of the derivative (of the waveform template with respect to phase) increases as smoothness K decreases. Thus in the family of waveform templates shown in FIGS. 3 and 4, each waveform is smoother than the waveform immediately to the left.

As the patient's ventilatory requirements increase, the smooth and comfortable waveform template changes to a progressively more square (and therefore more efficient, but generally less comfortable) waveform. In a preferred form, the pressure waveform template is a function of a smoothness variable K. When K=1.0, the template is smooth as shown in FIG. 1. When K=0.0, the template is a square wave, and intermediate values of K generate intermediate waveforms.

Figure 3:
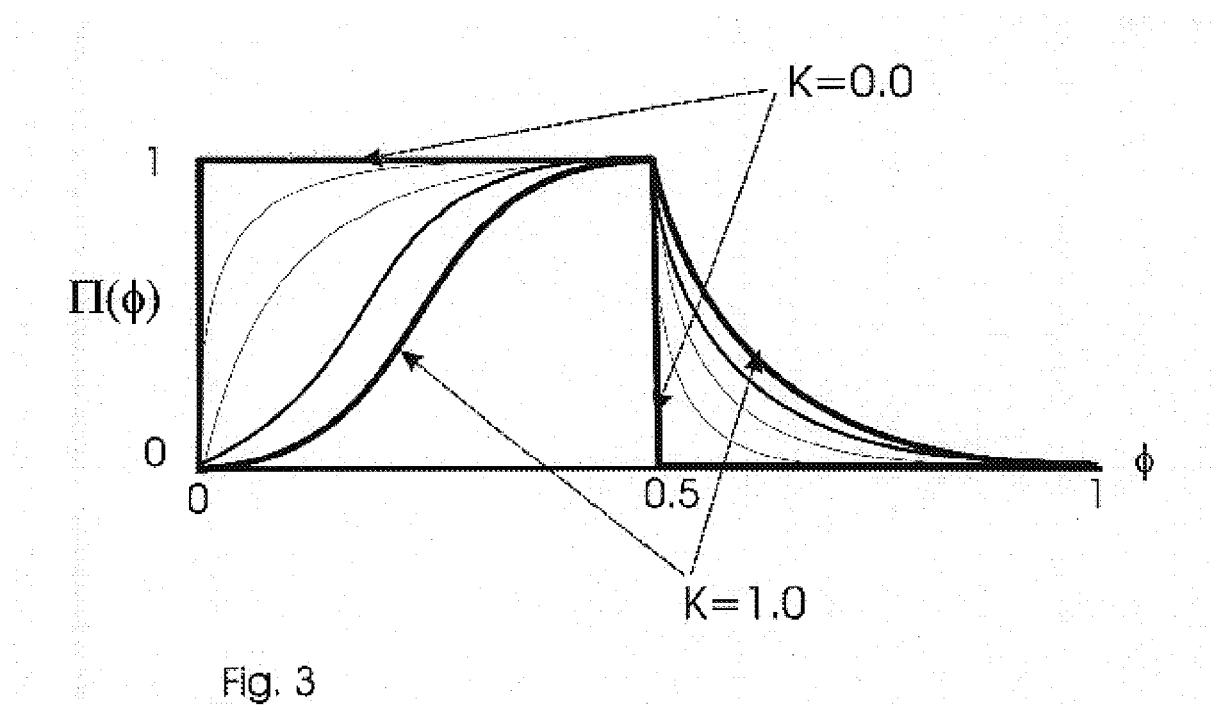
FIGS. 3 and 4 show two alternative variable templates for use in the apparatus of FIG. 2 in accordance with the invention, the shape of each template being a function of the instantaneous difficulty in ventilating the patient.

FIG. 3 shows one way in which the waveform can vary with K to generate intermediate waveforms. During inspiration, $\Pi(\Phi)$ is a blend between a raised cosine and a rising exponential, the time constant of the exponential decreasing with K. During expiration, $\Pi(\Phi)$ is a decaying exponential, also with a time constant that decreases as K increases. Letting, for K>0

$$u=0.5[1-\cos(2\pi\Phi)]$$

$$v=a(1-e^{-\Phi/K})$$

where $$a=1/(1-e^{-2.5/K})$$

we define $$\Pi(\Phi)=Ku+(1-K)v, \phi<0.5$$

$$\Pi(\Phi)=1-a(1-e^{-5(\Phi-0.5)/K}) \text{ otherwise.}$$

The equations degenerate to a square wave when K=0. The purpose of the constant a is to ensure that $\Pi(\Phi)$ approaches zero as $\Phi$ approaches 0.5 and also as $\Phi$ approaches unity.

As K decreases, two things happen to the inspiratory part of the curve: the exponential becomes progressively more like a rising step function, and the exponential contributes progressively more to the template, generating a family of curves intermediate between a raised cosine and a square wave. Similarly, as K decreases, the exponential in the expiratory part of the curve becomes more like a descending step function.

Figure 4:
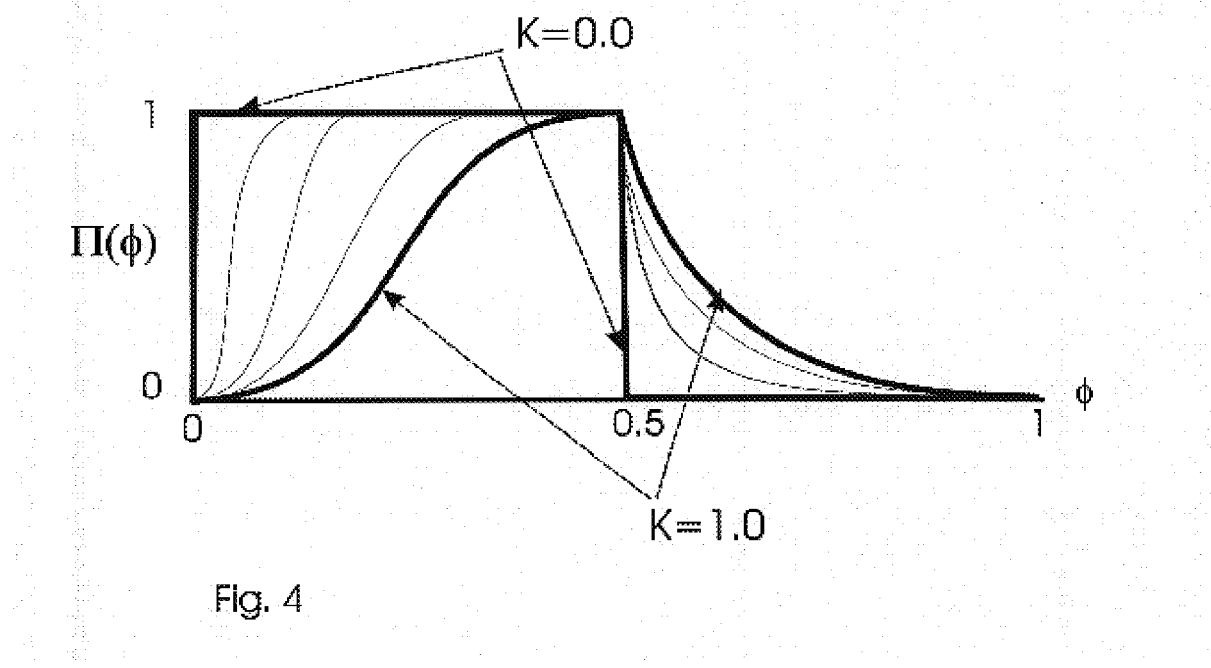

FIG. 4 shows another method, in which the inspiratory part of the curve is a raised cosine followed by a straight line:

$$\Pi(\Phi)=0.5[1-\cos(2\pi\Phi/K)], \phi<0.5, \phi<0.5 K$$

$$\Pi(\Phi)=1-a(1-e^{-5(\Phi-0.5)/K}), \phi>0.5$$

$$\Pi(\phi)=1, \text{ otherwise}$$

where $$a=1/(1-e^{-2.5/K})$$

In this method, with K=1.0, the straight line segment vanishes and the inspiratory curve is a raised cosine. As K decreases, the straight line segment lengthens and the raised cosine is squashed progressively to the left. Again, the equations degenerate to a square wave with K=0.0.

In both embodiments, the object is to use K=1.0 when small degrees of support are required, K=0.0 when very large degrees of support are required, and intermediate values of K in between.

In a simple form of the invention, K is adjusted in order to servo-control the patient's minute ventilation to equal a chosen target. For example, K may be adjusted using clipped integral control as follows:

$$K=G\int(0.5|f|-V_{TGT})dt, 0<=K<=1$$

where:

G is a gain, for example, 0.01 per L/min per second;

$V_{TGT}$ is the chosen target ventilation, for example, 7.5 L/min;

The reason for dividing the absolute value of the respiratory airflow by two is as follows. The target ventilation $V_{TGT}$ is specified with the units of L/min. Normally, ventilation is calculated as either the entire volume inspired per minute (inspired minute ventilation), or the entire volume expired per minute (expired minute ventilation). Equally, it can be calculated as the average of these two, in which case the average minute ventilation is half the average of the absolute value of the respiratory airflow over any given minute. More generally, the average ventilation is the average of half the absolute value of the respiratory airflow over any chosen period of time. Omitting the averaging step, we see that the instantaneous ventilation is half the absolute value of the respiratory airflow, and the term $0.5 |f|-V_{TGT}$ is the error in the instantaneous ventilation, and is therefore (on average) a measure of the adequacy of ventilation. If the term $0.5 |f|-V_{TGT}$ is on average positive, then the subject requires less ventilatory support, and conversely if it is on average negative, then the subject requires more ventilatory support. The clipped integral controller servo-controls this quantity to be zero on average, and therefore servo-controls the instantaneous ventilation to on average equal the target ventilation, whereupon the average ventilation also equals the target ventilation.

In this embodiment, if the subject is exceeding the target ventilation, the value of K will increase, yielding progressively smoother, more comfortable, but less efficient waveforms, until either the actual ventilation decreases to equal the target ventilation, or until K reaches 1.0, which yields the smoothest waveform. Conversely, if the subject is not achieving the target ventilation, K will decrease gradually, causing the waveform to become more square and more efficient, until either the target ventilation is achieved, or until K=0.0, representing a perfectly square waveform. For example, if K=1.0, $V_{TGT}$=7.5 L/min, G=0.01 per L/min per second, and the subject ceases all respiratory airflow, K will decrease to zero in 13.3 seconds.

There are two ways of increasing the degree of ventilatory support: using a more square waveform, and increasing the pressure modulation amplitude A. Therefore, in the present invention, both the smoothness K and the pressure modulation amplitude A may be adjusted, either simultaneously or sequentially, in order to achieve synergistically a desired target ventilation.

In a preferred form, a smooth waveform is used preferentially, and as far as possible the desired target ventilation is achieved by modulating the amplitude A, but if this is unsuccessful, then a progressively more square waveform is used, by decreasing K. In accordance with this form of the invention, the pressure modulation amplitude A may be adjusted using a clipped integral controller in order to servo-control minute ventilation to equal a desired target ventilation as follows:

$$A = -G \int (0.5|f| - V_{TGT}) dt, \quad 0 <= A_{MIN} <= A <= A_{MAX}$$

where:
G is a gain, for example, −0.3 cmH$_2$O per L/min per second;
$V_{TGT}$ is a chosen guaranteed minimum (target) ventilation, for example, 7.5 L/min;
$A_{MIN}$ is a minimum pressure modulation amplitude, chosen to make the patient comfortable while awake, for example, 3 cmH$_2$O; and
$A_{MAX}$ is a maximum pressure modulation amplitude, chosen to be sufficient to do all respiratory work, within the constraints of tolerability and safety, for example, 20 cmH$_2$O.

In the case where the patient's ventilation exceeds the target $V_{TGT}$, the pressure modulation amplitude A will reduce, until either the ventilation on average equals $V_{TGT}$ and A lies in the range $A_{MIN} < A < A_{MAX}$, or until A reaches $A_{MIN}$. Conversely, in the case where $A_{MAX}$ is insufficient to ventilate the patient at $V_{TGT}$, A will become equal to $A_{MAX}$.

In this preferred form, K is then calculated as a decreasing function of the pressure modulation amplitude A. In other words, as the pressure modulation amplitude A increases with the need for greater ventilatory support, K decreases to provide still further support (at the expense of comfort). Therefore, the pressure waveform template Π(Φ) becomes a function of the pressure modulation amplitude A. The invention delivers a comfortable, smooth pressure-vs-phase (and therefore pressure-vs-time) curve, providing the target ventilation $V_{TGT}$ is being achieved with a pressure modulation amplitude less than a chosen maximum $A_{MAX}$, but using a progressively more efficient, and therefore more square, waveform in the case where the target ventilation cannot be achieved using the chosen maximum.

To this end, the smoothness K may be calculated using clipped integral control using the following pseudocode:

```
K = 1.0
REPEAT every 20 milliseconds
    Calculate A
    IF A <A_MAX
        Increment K by 0.002
    ELSE
        Decrement K by 0.002
    END
    Truncate K to lie between 0.0 and 1.0
END
```

Initially, K=1.0, and the smoothest waveform will be used. In the case where the patient is being well ventilated at or above the target ventilation $V_{TGT}$, K will remain at 1.0 and the patient will continue to receive a very smooth and comfortable pressure waveform.

If the patient becomes difficult to ventilate, for example, due to sputum retention, failure of respiratory drive, diaphragm fatigue, failure of accessory muscles of respiration, mouth leak, or a large leak which is exceeding the capacity of the blower, K will gradually decrease towards zero.

The effect is that the actual delivered pressure waveform Π(Φ) changes gradually and continuously between the comfortable and smooth shape in FIG. 1, and a less comfortable but more efficient square wave. In the most severe case with ventilation remaining below $V_{TGT}$ and A remaining below $A_{MAX}$, K will reach zero in about 10 seconds, and a square wave will be delivered. In a less severe case, as K decreases and the waveform becomes progressively more square, and therefore more efficient at generating ventilation, $V_{TGT}$ will be achieved at an intermediate value of K and therefore at an intermediate waveform shape.

Should the conditions which led to the requirement for a more efficient waveform subside, the target ventilation $V_{TGT}$ will be met, pressure modulation amplitude will reduce to below $A_{MAX}$, and K will again increase, yielding a smoother and more comfortable waveform.

In the example given above, K increases at a maximum rate of 0.1 per second. Larger rates of change will produce a more rapid increase in effectiveness of ventilatory support, but are likely to lead to overshoot, with oscillations in the degree of support. Smaller rates of change will be stable, but will take longer to re-establish ventilation at $V_{TGT}$.

In the above algorithm, the ventilator attempts to cope with a need for increased ventilatory support in two discrete stages, first by increasing the pressure modulation amplitude, while maintaining the smooth waveform, but only up to a preset maximum amplitude $A_{MAX}$, and then subsequently by using a progressively more efficient waveform. In other embodiments it is possible for the two stages to overlap. For example, the pseudocode could be changed to:

```
K = 1.0
REPEAT every 20 milliseconds
    Calculate A
    Decrement K by 0.002(A - 0.75 A_MAX)
    Truncate K to lie between 0.0 and 1.0
END
```

This algorithm performs identically to the previous algorithm for the extreme cases of a patient who is either very difficult or very easy to ventilate, but differs for intermediate cases, because the transition from smooth to square begins earlier, at 75% of $A_{MAX}$. If more than 75% of the maximum pressure modulation is being used, K will decrease, and the waveform will become more square. Conversely, if more than 75% of the maximum pressure modulation is being used, K will increase and the waveform will become more rounded. Thus when increasingly ventilating the patient, it is possible to adjust the trade-off between increasing the pressure modulation amplitude and using a more efficient waveform.

In some cases, it may be desirable to prevent K from reaching zero. For example, keeping $0.1<K<1.0$ can produce almost as great an increase in efficiency at low K, but is more comfortable to the patient than a completely square waveform. This is particularly the case if large amounts of resistive unloading are used. (This is because a near-square waveform template on its own will produce a rapid increase in flow at start of inspiration, which will then produce yet further increase in pressure due to resistive unloading.)

Alternatively, K can be made to increase quickly at first, and then more slowly, so that the most square waveform is used only as a last resort, for example, by submitting K to a square root or similar transform. In other cases, with patients with considerable air hunger and intrinsic PEEP, it may be desirable to limit K to a value less than 1.0, although in general it would be preferable to increase the resistive unloading R and the end expiratory pressure $P_0$. In the above embodiments, K is related to the integral of A (minus a threshold) with respect to time, essentially using an integral controller to determine K, in an attempt to servo-control ventilation to equal or exceed $V_{TGT}$. In other embodiments, other known controllers such as PID controllers may be used.

Although the invention has been described with reference to particular embodiments, it is to be understood that these embodiments are merely illustrative of the application of the principles of the invention. In the above preferred embodiments, the pressure waveform is a function of phase in the respiratory cycle $\phi$, calculated as as taught in the commonly owned International Publication No. WO 98/12965 entitled "Assisted Ventilation to Match Patient Respiratory Need". However, if it is not desired to synchronize with the patient's spontaneous efforts, phase can be taken as increasing linearly with time at a preset rate, modulo 1 revolution. In this manner, the pressure waveform is a simple function of time, and the invention simplifies to modifying the shape of a fixed pressure-vs-time waveform. Thus, the pressure waveform may be a function of the phase in the patient's respiratory cycle, or time, or of both. Similarly, in the above preferred embodiments, linear resistive unloading is used, but the invention is applicable in the case of no resistive unloading, and also in the case of nonlinear resistive unloading. In the preferred embodiments described above, the pressure waveform template comprises a raised cosine followed by a quasi-exponential decay. However, the precise waveform is not overly critical. Waveforms with the broad general features of FIG. 1 are satisfactory, and will generally produce large improvements in comfort and synchronization over a square wave. The waveform may be modified to more or less precisely include eupneic resistive unloading by setting the waveform to be more or less closely the shape of the subject's eupneic transdiaphragmatic pressure vs phase curve. Again, in the preferred embodiments, a fixed non-zero end expiratory pressure is used, yet the invention extrapolates naturally to either zero end expiratory pressure or to automatically adjusted end expiratory pressure. Similarly, some specific examples of how to adjust the shape of the pressure waveform are given, but these are intended only as examples. In the examples given, both the inspiratory and expiratory phases of the pressure waveform template increase or decrease their smoothness. In the illustrative embodiments, a single parameter K defines the shape of the pressure waveform template. Also contemplated are embodiments in which more than one parameter defines the template. One example is to use one parameter for inspiration and another for expiration, and vary them independently. Another is to use one parameter which chiefly affects early inspiration and expiration, and another which chiefly affects late inspiration and expiration. Although the specific implementation delivers air from a blower, the invention works equally well with air, oxygen, or other breathable gases, and any source of breathable gas at controllable pressure may be used. Numerous other modifications may be made in the illustrative embodiments of the invention and other arrangements may be devised without departing from the spirit and scope of the invention.

What we claim is:

1. A method for controlling a pressure support servo ventilator comprising the steps of:
   supplying air to a patient's airway at a pressure that varies during each respiratory cycle, the pressure being characterized by both a pressure modulation amplitude and an adjustable pressure waveform template with a profile, and
   automatically controlling both said pressure modulation amplitude and the profile of said adjustable pressure waveform template by an output of a servo-controller operated to servo-control patient ventilation to at least equal a target value.

2. A method as in claim 1 in which said servo-controller increases a degree of support by at least one of increasing the pressure modulation amplitude and generating a pressure waveform that progressively becomes a square pressure waveform.

3. A method as in claim 1 in which said servo-controller decreases a degree of support by at least one of decreasing the pressure modulation amplitude and generating a pressure waveform that progressively becomes a smooth pressure waveform.

4. A method as in claim 1 in which the adjustable pressure waveform template is adjustable to a high degree of distinct waveform profiles between a smooth profile and a square profile.

5. A method as in claim 1 in which the profile of the adjustable pressure waveform template is adjusted to be smoother than a profile of a previous pressure waveform template if said pressure modulation amplitude is less than a threshold, and adjusted to be more square than a profile of a previous pressure waveform template otherwise.

6. A method for controlling a pressure support ventilator comprising the steps of:
   supplying air to a patient's airway at a pressure that varies during each respiratory cycle, the pressure being characterized by both a pressure modulation amplitude and a pressure waveform template of adjustable shape,
   deriving a measure of instantaneous patient ventilation, and
   automatically controlling both said pressure modulation amplitude and the shape of said pressure waveform template in accordance with said measure of instantaneous patient ventilation.

7. A method as in claim 6 in which the degree of ventilatory support is increased by at least one of increasing the pressure modulation amplitude and generating a progressively more square pressure waveform.

8. A method as in claim 6 in which a degree of ventilatory support is decreased by at least one of decreasing the pressure modulation amplitude and progressively generating pressure waveform templates that are smoother than a prior pressure waveform template.

9. A method as in claim 6 in which the pressure waveform template is adjustable to a high degree of different waveform shapes between a smooth shape and a square shape.

10. A method as in claim 6 in which the shape of said pressure waveform template is adjusted to be smoother than a shape of a previous pressure waveform template if said pressure modulation amplitude is less than a threshold, and adjusted to be more square than a shape of a previous pressure waveform template otherwise.

11. A pressure support ventilator comprising a supply of air for a patient's airway where a pressure of the supply of air varies during each respiratory cycle, the pressure being characterized by both a pressure modulation amplitude and an adjustable pressure waveform template with a profile, means for deriving a measure of instantaneous patient ventilation, and means for automatically controlling both said pressure modulation amplitude and said profile of said adjustable pressure waveform template in accordance with said measure of instantaneous patient ventilation.

12. A pressure support ventilator as in claim 11 in which a degree of ventilatory support is increased by at least one of increasing the pressure modulation amplitude and generating a pressure waveform that progressively approaches being a square waveform.

13. A pressure support ventilator as in claim 11 in which a degree of ventilatory support is decreased by at least one of decreasing the pressure modulation amplitude and progressively generating pressure waveform templates that are smoother than a prior pressure waveform template.

14. A pressure support ventilator as in claim 11 in which the profile of the adjustable pressure waveform template is adjustable to a high degree of waveform profiles between a smooth profile and a square profile.

15. A pressure support ventilator as in claim 11 in which said adjustable pressure waveform is adjusted to be smoother if said pressure modulation amplitude is less than a threshold, and adjusted to be more square otherwise.

16. A method for providing positive pressure ventilation comprising the steps of:
supplying a patient with breathable gas at a pressure which is a function of at least a measure of phase in a respiratory cycle, an amplitude, and a smoothness parameter;
determining a measure of ventilation of the patient; and
automatically adjusting said smoothness parameter within a preset range to servo-control said measure of ventilation to at least equal a target ventilation.

17. A method as in claim 16, in which said amplitude is adjusted within a preset range to servo-control said measure of ventilation to at least equal a target ventilation.

18. A method as in claim 17, in which said smoothness parameter is calculated from said amplitude.

19. A method as in claim 18, in which said servo-control is performed firstly by increasing or decreasing said amplitude, and secondarily adjusting said smoothness parameter if said amplitude is not within a specified range.

20. A pressure support ventilator comprising a supply of air for a patient's airway wherein a pressure of the supply of air is a function of at least a measure of phase in a respiratory cycle of the patient, an amplitude, and a smoothness parameter, wherein said smoothness parameter is a calculated function of a target ventilation, wherein, said amplitude is adjusted within a preset range to servo-control said ventilation to at least equal a target ventilation.

21. A pressure support ventilator as in claim 20, in which said smoothness parameter is calculated from said amplitude.

22. A pressure support ventilator as in claim 20, in which said servo-control is performed firstly by increasing or decreasing said amplitude, and secondarily adjusting said smoothness parameter if said amplitude is not within a specified range.

23. A method for controlling a degree of ventilatory support supplied to a patient by a pressure support ventilator, the method comprising the steps of
supplying breathable gas to a patient's airway by a pressure waveform having an adjustable amplitude and an adjustable squareness;
continuously determining a minute ventilation of the patient;
comparing the minute ventilation to a target ventilation;
If the minute ventilation is below the target ventilation, then first changing the adjustable amplitude to increase minute ventilation; and
if after increasing the minute ventilation it remains below the target ventilation, then making the waveform progressively more square.

24. The method of claim 23 wherein the adjustable amplitude is limited by a maximum amplitude, and wherein if the minute ventilation is below the target ventilation, then the adjustable amplitude is changed toward the maximum amplitude, and wherein if the minute ventilation is below the target ventilation and the adjustable amplitude exceeds a fraction of the maximum amplitude, then the pressure waveform is changed to become progressively more square.

25. The method of claim of 24 wherein the fraction is about 75%.

26. The method of claim 23 wherein the adjustable squareness of the pressure waveform is changes between a minimum and maximum and wherein at the maximum the pressure waveform is not completely square.

27. A method as claimed in claim 23 wherein the adjustable squareness of the pressure waveform changes between a minimum and maximum and wherein changes in waveform squareness near a squareness indicative of a completely square waveform take place more slowly than changes when the waveform is rounder.

28. A method of providing ventilatory support to a patient comprising the steps of:
supplying breathable gas to a patient's airway with a pressure waveform which has an adjustable squareness;
continuously determining minute ventilation;
comparing the minute ventilation to a target ventilation;
determining the presence of leak;
determining whether the leak is large; and
If the minute ventilation is below the target ventilation and the leak is large then gradually making the pressure waveform more square.

* * * * *